United States Patent
Hiyama et al.

(10) Patent No.: US 6,919,182 B2
(45) Date of Patent: Jul. 19, 2005

(54) METHOD OF DETECTING GENE AS AMPLIFIED PRODUCT BY GENE AMPLIFICATION AND REAGENT KIT THEREFOR

(75) Inventors: Kayo Hiyama, Kobe (JP); Koichi Yamagata, Kobe (JP); Makoto Ueda, Kakogawa (JP); Kadzuki Nakabayashi, Kobe (JP)

(73) Assignee: Sysmex Corporation, Hyogo (JP)

( * ) Notice: Subject to any disclaimer, the term of this patent is extended or adjusted under 35 U.S.C. 154(b) by 140 days.

(21) Appl. No.: 10/266,563

(22) Filed: Oct. 9, 2002

(65) Prior Publication Data

US 2003/0096284 A1 May 22, 2003

(30) Foreign Application Priority Data

Oct. 9, 2001 (JP) .................................... 2001-311601

(51) Int. Cl.⁷ ...................... C12Q 1/68; C12P 19/34; C07H 21/00; C07H 21/02; C07H 21/04
(52) U.S. Cl. ..................... 435/6; 435/91.1; 435/91.2; 536/23.1; 536/24.3; 536/24.32; 536/24.33
(58) Field of Search .................... 435/6, 91.1, 91.2; 536/23.1, 24.3, 24.32, 24.33

(56) References Cited

U.S. PATENT DOCUMENTS

| 5,176,995 A | 1/1993 | Sninsky et al. |
| 5,380,489 A | 1/1995 | Sutton et al. |
| 5,386,022 A | 1/1995 | Sninsky et al. |
| 5,622,822 A * | 4/1997 | Ekeze et al. ................... 435/6 |
| 5,747,256 A | 5/1998 | Yan et al. |
| 6,451,917 B1 | 9/2002 | Kogure et al. |

FOREIGN PATENT DOCUMENTS

| EP | 0 747 488 A1 | 12/1996 |
| JP | 4-67957 B2 | 10/1992 |
| JP | WO 01/83817 A1 | 11/2001 |

OTHER PUBLICATIONS

Sonja–Verena Albers et al.; Journal of Bacteriology, vol. 185, No. 13, Jul. 2003, pp. 3918–03925.
Tsugunori Notomi et al.; Nucleic Acids Research, 2000, vol. 28, No. 12, pp. i–vii.
G. Terrance Walker; Proc. Natl. Acad. Sci., vol. 89, pp. 392–396, Jan. 1992.
Yasuyoshi Mori et al.; Biochemical and Biophysical Research Communications, 289, pp. 150–154, 2001.

* cited by examiner

*Primary Examiner*—Jezia Riley
(74) *Attorney, Agent, or Firm*—Birch, Stewart, Kolasch & Birch, LLP

(57) ABSTRACT

A method of detecting a gene as an amplified product includes subjecting a solution containing the gene to a gene amplification reaction at a predetermined reaction temperature in the presence of a surfactant having a higher clouding point than the predetermined reaction temperature and detecting the gene as an amplified product, and a reagent kit for the method of detecting the gene as the amplified product utilizing the gene amplification includes a primer necessary for amplifying the gene, an enzyme for amplifying the gene, and a surfactant having a clouding point higher than the predetermined reaction temperature, wherein the primer is packed separately from the enzyme, and the surfactant is packed with the primer or the enzyme, or separately.

13 Claims, 3 Drawing Sheets

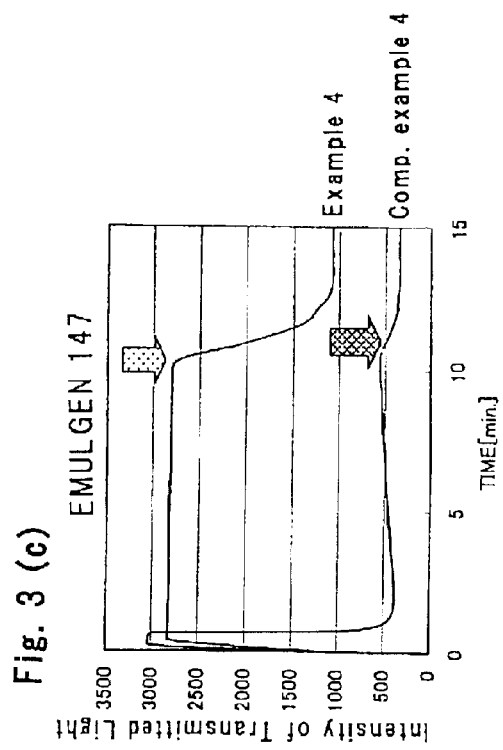
Fig. 3 (a) EMULGEN 220
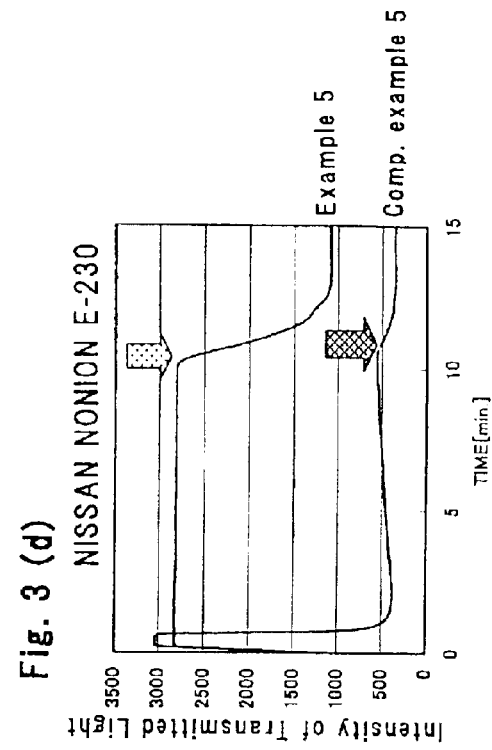
Fig. 3 (b) EMULGEN 123P
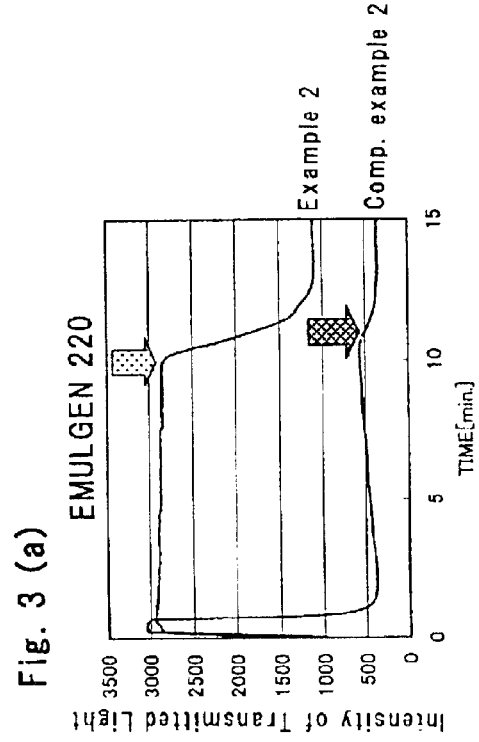
Fig. 3 (c) EMULGEN 147
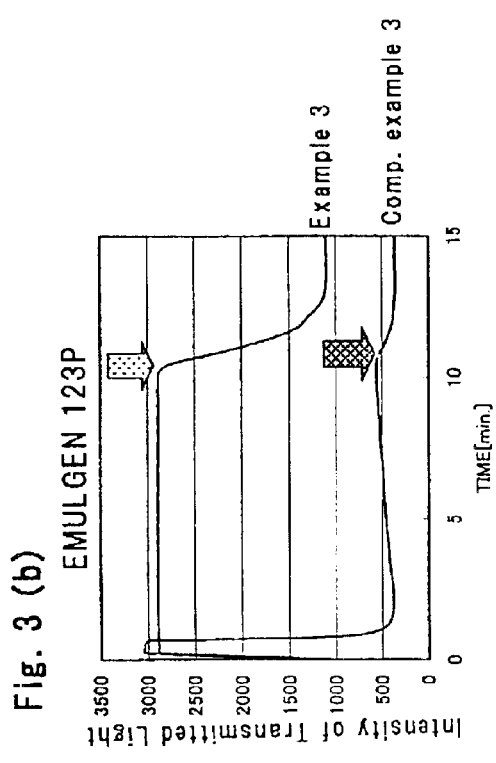
Fig. 3 (d) NISSAN NONION E-230

METHOD OF DETECTING GENE AS AMPLIFIED PRODUCT BY GENE AMPLIFICATION AND REAGENT KIT THEREFOR

CROSS-REFERENCE TO RELATED APPLICATION

This application is related to Japanese application No. 2001-311601 filed on 9 Oct., 2001, whose priority is claimed under 35 USC §119, the disclosure of which is incorporated by reference in its entirety.

BACKGROUND OF THE INVENTION

1. Field of the Invention

The present invention relates to a method of detecting a gene as an amplified product by gene amplification and a reagent kit for the method, more particularly, a method for accurately detecting a gene as an amplified product or a byproduct by reducing the turbidity which is generated in a gene amplification solution and may disturb accurate detection of the gene or the byproduct and a reagent kit for the method.

2. Description of Related Art

A variety of gene amplification methods are effectively utilized in identification of genetic diseases, cancer, microorganisms or the like in medical scenes and others, because of their simplicity and rapidity. Among such methods, PCR (polymerase chain reaction) is often used particularly in the medical field since the method is good in sensitivity (Japanese patent publication HEI 4(1992)-67957). Also, attention is being given to a LAMP (Loop-mediated Isothermal Amplification) method because this method provides a specific reaction and can amplify a large amount of an amplified product (Japanese patent 3313358).

Further, in recent years, a quantitative PCR method has been developed which enables determination of the amount of existing target genes as well as amplification of target genes. According to this method, the degree of the amplification of the target genes can be detected in real time fashion and the amount of the target genes can be determined with respect to the time when amplification is detected.

The real-time detection of gene amplification is roughly classified into two types, i.e., a fluorescent method and a turbidimetric method. Particularly, according to the turbidimetric method, quantitative gene amplification can be performed by detecting amplified products in real time fashion with use of a precipitation as a turbidity index. The precipitation is produced in a solution by reaction of magnesium with pyrophosphoric acid which is generated by gene amplification. Furthermore, a detector used for the turbidimetric method is simple. In these respects, the turbidimetric method is superior.

However, solution for gene amplification typically contains not only enzymes such as polymerase, reverse transcriptase and the like but also surfactants for improving the stability and reactivity of the enzymes. If amplification reaction is carried out with use of such solution with heating to about 65° C., the solution become turbid owing to the surfactants. For this reason, in the medical scene or the like, when the amplification of target genes is detected by the turbidimetric method, the background from the solution increase, and therefore, it is impossible to detect the gene amplification with high sensitivity and accuracy.

SUMMARY OF THE INVENTION

The present invention has been made in view of the above-mentioned problems, and an object of the invention is to provide a method of detecting a gene, which method allows suppression of turbidity owing to the heating of the solution, and to provide a reagent kit for the method.

Accordingly, the present invention provides a method of detecting a gene as an amplified product, i.e., detecting an amplified product including subjecting a solution containing the gene to a gene amplification reaction at a predetermined reaction temperature in the presence of a surfactant having a higher clouding point than the predetermined reaction temperature; and detecting the gene as the resulting amplified product.

Further, the present invention provides a method of detecting a gene as an amplified product including adding a second surfactant to a solution containing the gene and a first surfactant having a clouding point lower than a predetermined reaction temperature of a gene amplification reaction in order to raise the clouding point of the solution higher than the predetermined reaction temperature; subjecting the solution to the gene amplification reaction at the predetermined reaction temperature; and optically detecting the gene as the resulting amplified product.

Moreover, the present invention provides a reagent kit for the method of detecting a gene as an amplified product utilizing gene amplification, the reagent kit including a primer necessary for amplifying the gene; an enzyme for amplifying the gene; and a surfactant having a clouding point higher than a gene amplification reaction temperature, wherein the primer are packed separately from the enzyme, and the surfactant is packed with the primer or the enzyme, or separately.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 3(a) to 3(d) are graphical representations showing output values with respect to time in other examples of the method of detecting a gene as amplified product in accordance with the present invention.

DESCRIPTION OF THE PREFERRED EMBODIMENTS

The method of detecting a gene as an amplified product of the present invention is used for detection of the presence or absence of a gene product synthesized utilizing gene amplification and is applicable to any method of analyzing, measuring or detecting the presence or absence of a synthesized gene product with use of an optical technique. More particularly, the invention can be applied to various methods such as a method of detecting turbidity, a method of detecting absorbency, a method of detecting scattered light intensity, a method of detecting fluorescence intensity and the like. Among these methods, the invention may preferably be applied to the methods of detecting turbidity and scattered light intensity.

Figure 1:
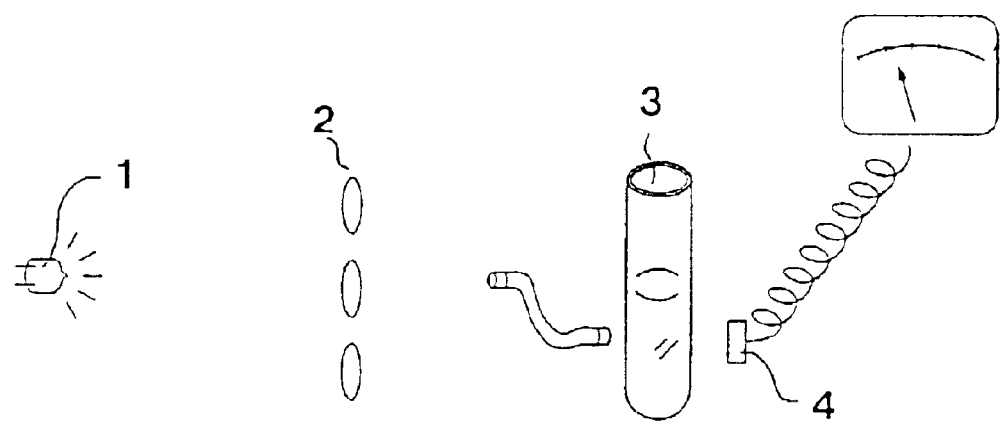
FIG. 1 illustrates the principle of a turbidity detector used in the method of detecting a gene as amplified product in accordance with the present invention.

The amplified product may be detected with use of light having a wavelength of about 310 nm to about 1285 nm, more particularly, light having a wavelength of 400 nm, 405 nm, 575 nm, 800 nm or the like. The turbidity and the scattered light may be detected, for example, as shown in FIG. 1, by taking out light having a desired wavelength from light emitted from a light source 1 through a filter 2, applying the taken-out light to an object 3 to be detected, detecting light transmitted or scattered by the object 3 using a photoreceptor 4 and optionally converting the detected light into an electrical signal.

Examples of gene amplification methods include a variety of methods such as LAMP (Notomi, T. et. al.,: Nucleic acids Res. 28:e63, 2000), LCR, SDA, NASBA, RCA, ICAN, TMA, quantitative PCR, modifications of these methods. Among these methods, if the turbidity or the scattered light is intended to be detected, the LAMP method may preferably be used.

In gene amplification methods, typically, an enzymatic reaction takes place in a solution for amplifying a gene. The solution may usually contain a buffer for providing a suitable pH for the enzymatic reaction, a salt necessary for maintaining the enzymatic activity of an enzyme, a surfactant (a first surfactant) for protecting and stabilizing the enzyme, a diluent, a substance for suppressing non-specific reaction and a sensitizer, and the like. Also a gene to be amplified, a primer, an enzyme and the like are mixed in the solution. Thus the solution is ordinarily prepared.

According to the method of detecting a gene of the present invention, a surfactant (a second surfactant) other than the surfactant (the first surfactant) essentially contained in the solution is added to the solution in order to raise the clouding point of the solution. It should be noted that the order of mixing these components of the solution is not particularly limited. The type and concentration of the buffer, salt, surfactant and the like in the solution may be selected as appropriate depending upon the type of the gene to be amplified, the primer and the enzyme. Also the gene to be amplified, the primer, the enzyme and the like may be selected as appropriate depending upon a gene amplification method to be utilized, the type and amount of the gene, the primer and the enzymes, and others.

For example, as buffers, those having a buffer action from neutrality to weak alkalescence such as Tris-HCl may be mentioned. As salts, KCl, NaCl, $(NH_4)_2SO_4$ and the like may be mentioned. The surfactant (the first surfactant) is required to do no damage to the enzyme and be capable of retaining the steric structure of the enzyme and keeping the enzyme stable. A nonionic surfactant as mentioned below, usually alkylarylpolyethylene glycol (Triton X-100), may be used as the surfactant, but any nonionic surfactant may be used in place of Triton X-100. Since it has a clouding point lower than the reaction temperature of gene amplification reaction as described later, Triton X-100 causes clouding during the gene amplification reaction.

The surfactant added further to the solution, i.e., the second surfactant, is required to be capable of raising the clouding point of the solution (the clouding point is due mainly to the surfactant essentially contained in the solution) higher than the reaction temperature of the gene amplification reaction described later. Further the second surfactant is also required to do no damage to the enzyme and be capable of keeping the enzyme stable. The second surfactant may be selected as appropriate depending upon the type and amount of the surfactant essentially contained in the solution and the type and amount of the gene, the primer and the enzyme which are used. Generally, the second surfactant advantageously has a clouding point higher than the reaction temperature.

As the second surfactant, may be mentioned one having a clouding point of 70° C. or higher, for example. As such surfactants, may be mentioned EMULGEN 220 (produced by Kao Corporation) having a clouding point of 98° C., and TERGITOL NP-40 (produced by Sigma), EMULGEN 123P (produced by Kao Corporation), EMULGEN 147 (produced by Kao Corporation) and NISSAN NONION E-230 (produced by Nippon Yushi KK) which have a clouding point of 100° C. or higher.

The second surfactant may preferably be a nonionic surfactant among various kinds of surfactants. More particularly, examples of the second surfactant may include:

(1) fatty acid esters of polyoxy compounds such as
   glycerin higher fatty acid esters (e.g., glyceride monostearate, glyceride monooleate, etc.);
   glycol fatty acid esters (e.g., polyglycol stearate, diethylene glycol laurate, propylene glycol monolaurate, propylene glycol monooleate, propylene glycol monostearate, polyethylene glycol alkyl ether, polyethylene glycol alkenyl ether, etc.);
   pentaerythritol fatty acid esters (e.g., pentaerythritol monostearate, pentaerythritol monocaprylate, pentaerythritol soy bean fatty acid ester, pentaerythritol monolaurate, etc.);
   sucrose fatty acid esters (e.g, sucrose laurate, sucrose myristate, sucrose palmitate, etc.);
   sorbitan and mannitan fatty acid esters (e.g., sorbitan sesquioleate, sorbitan monolaurate, a condensation product of sorbitan monolaurate with polyethylene oxide, mannitan monooleate, a condensation product of mannitan monopalmitate with polyethylene oxide, etc.);

(2) polyethylene oxide condensation products such as
   higher alcohol condensation products (polyoxyethylene alkyl ether, (e.g., hexadecynol, dodecanol polyethylene oxide, etc.), polyoxyethylene alkenyl ether (e.g., oleinol polyethylene oxide, etc.), fatty acid alcohol polyethylene glycol ether, polyethylene glycol alkylphenyl ether, etc.);
   higher fatty acid condensation products (e.g., a condensation product of a monolaurate with polyethylene oxide, a condensation product of a ricinoleate with polyethylene oxide, etc.);
   higher fatty acid condensation products with amides;
   higher alkyl condensation products with amines;
   higher alkyl condensation products with mercaptans;
   alkylphenol condensation products (a polyoxyethylene alkylphenyl ether, nonylphenol polyoxyethylene ether, a condensation product of alkylallyl ethers with polyethylene oxide, a condensation product of diaminophenol ether with polyethylene oxide, a condensation product of an alkylphenol ether with polyethylene oxide, etc.);
   polypropylene oxide condensation products (e.g., polyoxypropylene glycol, etc.).

Among these surfactants, polyoxyethylene-base surfactants are preferred. The additional molar number of ethylene oxide may be about 10 to 100. Particular examples of such surfactants are represented by the following formula:

wherein $R_1$ is $C_{8-22}$ alkyl or alkenyl, $R_2$ is —O—, —($C_6H_4$)—O— or —COO— and n is an integer of 10 to 100.

The $C_{8-22}$ alkyl may be of straight chain or branched, including octyl, nonyl, dodecyl (lauryl), hexadecyl and the like, for example. The $C_{8-22}$ alkenyl may be of straight chain or branched, including octenyl, oleyl, hexadecenyl and the like, for example. $C_6H_4$ is an aromatic ring.

Preferably, the second surfactant is used in such an amount that the clouding point of the solution is raised above the reaction temperature, clouding is suppressed and specific gene amplification reaction is not affected. The amount may be selected as appropriate depending upon the type and amount of the surfactant essentially contained in the solution and the type and amount of the gene, the primer and the enzyme which are used. For example, the amount of the second surfactant may be about 0.1 to 20 times, preferably about 0.1 to 10 times, most preferably about 0.5 to 2 times larger in weight than the amount of the surfactant essentially contained in the solution. Particularly, where Triton-X and TERGITOL NP-40 are used together in the solution, the proportion of Triton-X to TERGITOL NP-40 may preferably be 0.1 wt %: 0.01 wt % to 2.0 wt %. From another point of view, the second surfactant may be added in a proportion of preferably about 0.05 to 10.0 wt %, more preferably about 0.1 to 1.0 wt %, with respect to the solution.

The gene amplification reaction can be carried out either by isothermal reaction or by temperature cycling reaction. The gene amplification reaction temperature is preferably within the range from the reaction temperature of a TMA method, i.e., 40° C., which is the lowest among the gene amplification methods to the reaction temperature of PCR method, i.e., 95° C., which is the highest thereamong, i.e., from 40 to 95° C.

For example, in the isothermal reaction, the solution is heated to a suitable temperature, which is maintained for a suitable time period. The reaction is usually carried out by heating the solution to about 40 to 70° C. and maintaining about 10 minutes to about 3 hours. However, a reaction at another temperature can be added before or after the isothermal reaction.

In the temperature cycling reaction, the gene amplification is performed by repeating the cycle of heating the solution, for example, to 95° C. for a minute, to 55° C. for a minute and to 72° C. for a minute 15 to 40 times. However, a reaction at another temperature can be added before or after the temperature cycling reaction.

In the present invention, the gene amplification reaction temperature means not only the temperature of the actual amplification reaction but also the temperature of detecting the product by the gene amplification reaction. It is preferable that the temperature of the gene amplification reaction equals to the temperature of detection of the product by gene amplification, but these temperatures are not necessarily the same.

In the isothermal reaction or the temperature cycling reaction, the presence of the product of the gene amplification can be detected by applying an optical technique, for example. Such optical techniques include those mentioned above.

Various reagent components required for the method of detecting the gene product by the gene amplification of the present invention may be packaged into a kit. More particularly, there is provided a reagent kit including a primer necessary for amplifying a gene, an enzyme for amplifying the gene and a surfactant having a clouding point higher than the gene amplification reaction temperature and further, if required, a salt necessary for annealing, a diluent and a buffer for providing a suitable pH for an enzymatic reaction, and optionally, a substance for suppressing a non-specific reaction and a sensitizer. The primer is preferably packed separately from the enzyme. The surfactant is packed with the primer or the enzyme, or separately. Also the surfactant is packed with one or more other components, or separately. The components other than the primer, the enzyme and the surfactant may be packed with the primer or the enzyme, or may be packed separately.

The method of detecting a gene product of the present invention is described in detail below.

EXAMPLE 1

First, a CA-6000 reaction tube (manufactured by Sysmex Corporation) was placed on ice and a solution was prepared.

| Solution | |
|---|---|
| Water | 52.0 μL |
| 10X Thermopol buffer (manufactured by NEB (New England Biolabo)) | 20.0 μL |
| 10 mM dNTPs (manufacture by GIBCO) | 8.0 μL |
| 100 mM MgSO₄ (manufactured by NEB) | 4.0 μL |
| 5 M betaine (manufactured by Sigma) | 32.0 μL |
| FA primer (40 pmol/μL)) | 8.0 μL |
| RA primer (40 pmol/μL)) | 8.0 μL |
| F3 primer (5 pmol/μL)) | 8.0 μL |
| R3 primer (5 pmol/μL)) | 8.0 μL |

The 10X Thermopol buffer was composed of
(strikethrough: 20 mM) 200 mM Tris-HCl pH8.8,
(strikethrough: 10 mM) 100 mM KCl,
(strikethrough: 10 mM) 100 mM $(NH_4)_2SO_4$,
(strikethrough: 2 mM) 20 mM $MgSO_4$ and
(strikethrough: 0.1%) 1.0% Triton X-100 (clouding point : 63 to 69° C.).

The primers were single-stranded DNAs, having the following nucleotide sequences:

```
FA primer
ACAACGTCGTGACTGGGAAAACCCTTTTTGTGCGGGCCTCTTCGCTATTA
C;

RA primer
CGACTCTAGAGGATCCCCGGGTACTTTTTGTTGTGTGGAATTGTGAGCGG
AT

F3 primer
GTTGGGAAGGGCGATCG

R3 primer
ACTTTATGCTTCCGGCTCGTA
```

To this reaction solution, 20 μL of 1.0% TERGITOL NP-40 (nonyl phenol polyoxyethylene ether, the number of oxyethlene: 40, clouding point: more than 100° C., produced by Sigma) was added, followed by stirring.

Subsequently, 16.0 μL of Bst DNA polymerase large fragment (produced by NEB) and 16.0 μL of M13 mp18 DNA (produced by Takara) as a template was added, followed by stirring.

Then, the reaction tube was transferred to an apparatus (an improved version of CA-1500) equipped with a detection section using light of 400 nm wavelength as shown in FIG. 1. The reaction tube was inserted in a heat block at 65° C. which allowed the solution to be maintained at 65° C. Immediately after the reaction tube was inserted into the heat block after the mixture of the solution, the turbidity of the solution was measured in real time fashion and the amplification of the gene was detected on the basis of changes in transmitted light.

As a comparative example, the above-described solution was reacted in the same manner as described above except that 1.0% TERGITOL NP-40 was not added, and the turbidity of the solution was measured.

Figure 2:
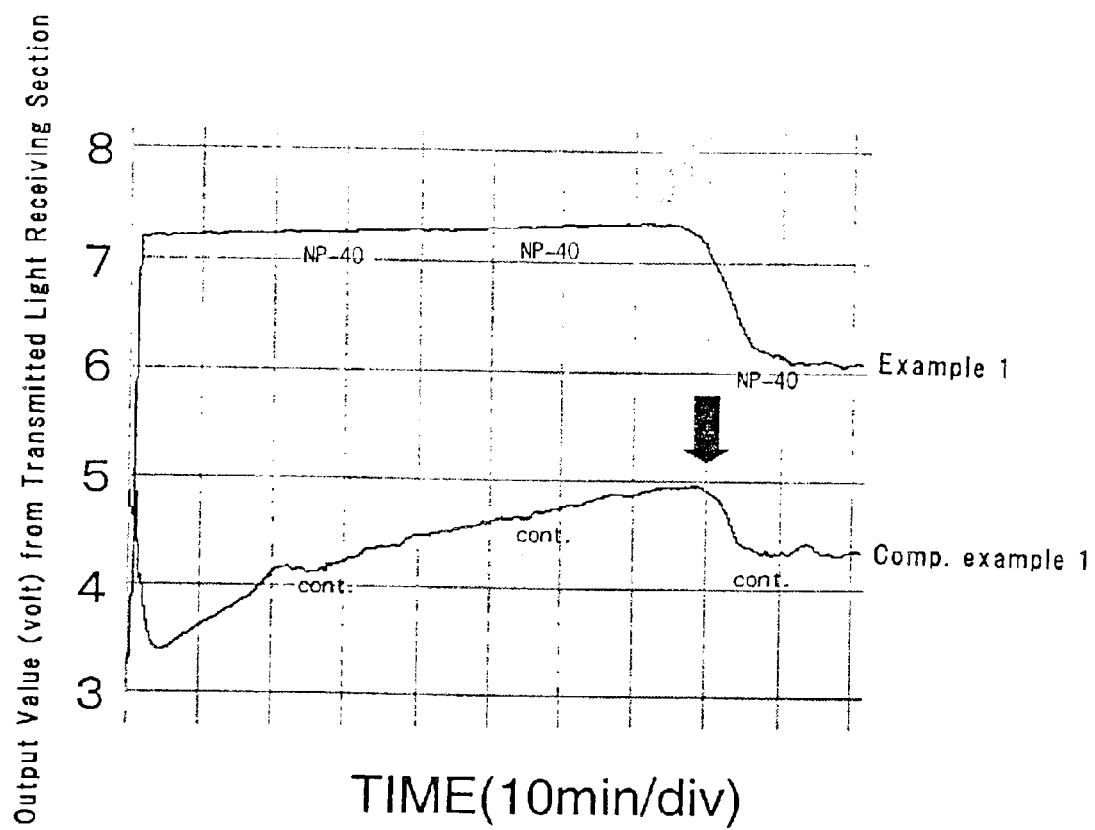
FIG. 2 is a graphical representation showing output values with respect to time in an example of the method of detecting a gene as amplified product in accordance with the present invention.

The results are shown in FIG. 2.

According to FIG. 2, the addition of 1.0% TERGITOL NP-40 raised the clouding point of the solution (mainly the clouding point attributed to the surfactant inherently contained in the solution) to 70° C. or above, and thereby the clouding of the solution was suppressed. Accordingly, the background was able to be kept stable in measurement of the intensity of transmitted light (an output value (volt) from a transmitted light receiving section). The intensity of the transmitted light was also able to be kept stable after the beginning of the reaction indicated by an arrow. Further, the point of the beginning of the reaction indicated by the arrow was clearly recognized, which enabled accurate detection of the presence of the product by the gene amplification. On the other hand, in the case where 1.0% TERGITOL NP-40 was not added, variations in the background were observed in the measurement of the intensity of transmitted light. Variations were also observed in the intensity of the transmitted light after the beginning of the reaction.

EXAMPLES 2 to 5

First, a CA-6000 reaction tube (manufactured by Sysmex Corporation) was placed on ice and a solution was prepared. To the solution, 20 µL of mRNA of cytokeratin 20 were added as template, followed by stirring.

The reaction tube was placed in a detection section of a detection apparatus at 65° C. to start gene amplification reaction. The intensity of transmitted light was detected in real time fashion, and the turbidity was checked.

As a comparative example, the solution was prepared without adding the surfactant and subjected to the same reaction. The turbidity of the solution was checked.

| Solution | |
|---|---|
| Water | 7.5 µL |
| 422 mM Tris-HCl pH 8.0 (manufactured by KK Nippon Gene) | 14.2 µL |
| 10X Thermopol buffer (manufactured by NEB) | 10.0 µL |
| 10 mM dNTPs (manufacture by Invitrogen) | 4.0 µL |
| 100 mM MgSO₄ (manufactured Sigma) | 4.0 µL |
| 0.1 M DTT (Wako Junyaku Kogyo KK) | 5.0 µL |
| 5 M betaine (manufactured by Sigma) | 12.8 µL |
| FA primer (40 pmol/µL) | 4.0 µL |
| RA primer (40 pmol/µL) | 4.0 µL |
| F3 primer (5 pmol/µL) | 4.0 µL |
| R3 primer (5 pmol/µL) | 4.0 µL |
| Loop primer Forward (20 pmol/µL) | 4.0 µL |
| Loop primer Reverse (20 pmol/µL) | 4.0 µL |
| 10% surfactant | 10.0 µL |
| 10 U/µL AMV reverse transcriptase (manufactured by Promega Co.) | 0.5 µL |
| 8000 U/mL Bst DNA polymerase large fragment (manufactured by NEB) | 8.0 µL |

The primers were single-stranded DNAs, having the following nucleotide base sequences:

```
FA primer
CAATTTGCAGGACACACCGAGATTGAAGAGCTGCGAAGTC;

RA primer
CTGCTGAGGACTTCAGACTGACTGACTTGGAGATCAGCTTCCAC;

F3 primer
CGACTACAGTGCATATTACAGAC;

R3 primer
GTAGGGTTAGGTCATCAAAGAC;

Loop primer Forward
GCAGTTGAGCATCCTTAATCT; and

Loop primer Reverse
GACTGCGCGCGGAATACGTC.
```

The following four types of surfactants were used.

Emulgen 123P (polyoxyethylenelauryl ether, oxyethylene number: 23, manufactured by Kao Corporation)

Emulgen 147 (polyoxyethylenelauryl ether, oxyethylene number: 19, manufactured by Kao Corporation)

Emulgen 220 (polyoxyethylenecetyl ether, oxyethylene number: 13, manufactured by Kao Corporation)

Nissan nonion E-230 (polyoxyethyleneoleyl ether, oxyethylene number: 30, manufactured by Nippon Yushi KK).

An apparatus (MU001, Sysmex Corporation) equipped with a detection section using light of 400 nm wavelength and having the same principle as the apparatus shown in FIG. 1 was used as a detection apparatus. This apparatus can measure the intensity of transmitted light in real time fashion immediately after the reaction tube is inserted in the detection section of a heat block at 65° C.

The intensity of transmitted light is obtained by A/D converting an electric signal output by a light receptive element 4 as shown in FIG. 1 in response to receipt of transmitted light.

The obtained results are shown in FIGS. 3(A) to 3(D). According to these figures, the addition of the surfactants raised the clouding point of the solution to 70° C. or above. Thereby clouding of the solution was suppressed, the background was able to be kept stable in measurement of the intensity of transmitted light. The intensity of the transmitted light was also able to be kept stable after the beginning of the reaction indicated by an arrow. Further, the point of the beginning of the reaction indicated by the arrow was clearly recognized, which enabled accurate detection of the presence of the product by the gene amplification. On the other hand, in the case where the surfactants were not added, variations in the background were observed in the measurement of the intensity of transmitted light. Variations were also observed in the intensity of the transmitted light after the beginning of the reaction.

According to the present invention, the addition of the surfactant to the solution can prevent the occurrence of clouding, which is due to the surfactant essentially contained in the solution. Therefore, the background can be reduced and stabilized in the optical detection of the amplified gene without the specific amplification reaction being affected. Thus the presence of the amplified gene product can be detected with improved accuracy.

What is claimed is:

1. A method of detecting a gene as an amplified product comprising:

preparing a solution comprising the gene, an enzyme for amplifying the gene and a nonionic polyoxyethylene surfactant having a clouding point of 70° C. or higher;

subjecting the solution to a gene amplification reaction at a predetermined reaction temperature; and detecting the gene as an amplified product, wherein the clouding point of the nonionic polyoxyethylene surfactant is higher than the predetermined reaction temperature.

2. A method according to claim 1, wherein the nonionic polyoxyethylene surfactant is represented by the following formula:

$$R_1-R_2-(CH_2CH_2O)_n-H$$

wherein $R_1$ is $C_{8-22}$ alkyl or alkenyl, $R_2$ is —O—, —($C_6H_4$)—O— or —COO— and n is an integer of 10 to 100.

3. A method according to claim 1, wherein the predetermined reaction temperature is 40° C. to 95° C.

4. A method according to claim 1, wherein the surfactant is added to the solution in a proportion of 0.05 wt % to 10 wt % with respect to the solution.

5. A method of detecting a gene as an amplified product comprising:

preparing a solution comprising the gene, a first surfactant and a second surfactant;

subjecting the solution to a gene amplification reaction at a predetermined reaction temperature; and detecting the gene as an amplified product, wherein the first surfactant has a clouding point lower than the predetermined reaction temperature of the gene amplification reaction and the second surfactant has a clouding point higher than the predetermined reaction temperature of the gene amplification reaction.

6. A method according to claim 5, wherein the second surfactant has a clouding point of 70° C. or higher.

7. A method according to claim 5, wherein the surfactant is a nonionic polyoxyethylene surfactant.

8. A method according to claim 5, wherein the second surfactant is added to the solution in a proportion of 0.05 wt % to 10 wt % with respect to the solution.

9. A method according to claim 7, wherein the nonionic polyoxyethylene surfactant is represented by the following formula:

$$R_1-R_2-(CH_2CH_2O)_n-H$$

wherein $R_1$ is $C_{8-22}$ alkyl or alkenyl, $R_2$ is —O—, —($C_6H_4$)—O— or —COO— and n is an integer of 10 to 100.

10. A method according to claim 5, wherein the predetermined reaction temperature is 40° C. to 95° C.

11. A method according to claim 5, wherein the gene is detected as the amplified product by a turbidity of the solution.

12. A method of detecting a gene as an amplified product comprising:

preparing a solution comprising the gene, an enzyme for amplifying the gene and a nonionic surfactant having a clouding point of 70° C. or higher;

subjecting the solution to a gene amplification reaction at a predetermined reaction temperature; and detecting the gene as an amplified product by turbidity of the solution, wherein the clouding point of the nonionic surfactant is higher than the predetermined reaction temperature.

13. A method of detecting a gene as an amplified product comprising:

preparing a solution comprising the gene, an enzyme for amplifying the gene and a nonionic surfactant having a clouding point of 70° C. or higher;

subjecting the solution to a gene amplification reaction at a predetermined reaction temperature; and detecting the gene as an amplified product by at least one of turbidity, absorbency, scattered light intensity and fluorescence intensity of the solution, wherein the clouding point of the nonionic surfactant is higher than the predetermined reaction temperature.

* * * * *